(12) United States Patent
Jo et al.

(10) Patent No.: US 11,130,721 B2
(45) Date of Patent: Sep. 28, 2021

(54) METHOD FOR COLLECTING HARD OLEFIN

(71) Applicant: HYOSUNG CHEMICAL CORPORATION, Seoul (KR)

(72) Inventors: Bu Young Jo, Anyang-si (KR); Won Il Kim, Seongnam-si (KR); Jae Han Cho, Seoul (KR); Jae Young Woo, Seongnam-si (KR); Hee Chul Yeom, Anyang-si (KR); Dan Bi Chung, Anyang-si (KR); Min Jung Cho, Anyang-si (KR)

(73) Assignee: Hyosung Chemical Corporation, Seoul (KR)

( * ) Notice: Subject to any disclaimer, the term of this patent is extended or adjusted under 35 U.S.C. 154(b) by 121 days.

(21) Appl. No.: 16/617,253

(22) PCT Filed: Jul. 18, 2017

(86) PCT No.: PCT/KR2017/007707
§ 371 (c)(1),
(2) Date: Nov. 26, 2019

(87) PCT Pub. No.: WO2018/221785
PCT Pub. Date: Jun. 12, 2018

(65) Prior Publication Data
US 2021/0130263 A1 May 6, 2021

(30) Foreign Application Priority Data
Jun. 1, 2017 (KR) .......................... 10-2017-0068633

(51) Int. Cl.
*C07C 5/333* (2006.01)
*C07C 7/12* (2006.01)
(Continued)

(52) U.S. Cl.
CPC ............ *C07C 5/333* (2013.01); *B01D 53/047* (2013.01); *C01B 3/56* (2013.01); *C07C 7/005* (2013.01);
(Continued)

(58) Field of Classification Search
None
See application file for complete search history.

(56) References Cited

U.S. PATENT DOCUMENTS 3,437,703 A * 4/1969 Mayfield .................. C07C 5/48
585/443
4,121,917 A * 10/1978 Baker ....................... C07C 7/11
62/630
(Continued)

FOREIGN PATENT DOCUMENTS

KR 10-2007-0093445 A 9/2007
KR 10-2008-0015104 A 2/2008
(Continued)

OTHER PUBLICATIONS

International Search Report and Written Opinion, International Patent Application No. PCT/KR2017/007707, dated Oct. 5, 2018, with English translation of Search Report (11 pages).

*Primary Examiner* — Tam M Nguyen
(74) *Attorney, Agent, or Firm* — Hamre, Schumann, Mueller & Larson, P.C.

(57) ABSTRACT

The present invention relates to a method for recovering light olefins, which can achieve an increase in propylene production and a reduction in the basic unit of a process by feeding steam into five serially connected dehydrogenation reactors, and can diversify the product of a propane dehydrogenation reaction process from a propylene single product into propylene and ethylene by separately collecting ethane and ethylene, i.e., by-products of the propylene (Continued)

production process, and converting the ethane into ethylene, thereby improving the economic efficiency of the process and selectivity.

13 Claims, 2 Drawing Sheets

(51) Int. Cl.
    *B01D 53/047*     (2006.01)
    *C01B 3/56*     (2006.01)
    *C07C 7/00*     (2006.01)
    *C07C 7/04*     (2006.01)

(52) U.S. Cl.
    CPC ................ *C07C 7/04* (2013.01); *C07C 7/12* (2013.01); *B01D 2256/16* (2013.01); *B01D 2257/502* (2013.01); *C01B 2203/042* (2013.01); *C01B 2203/062* (2013.01); *C01B 2210/0014* (2013.01)

(56) References Cited

U.S. PATENT DOCUMENTS

| | | | |
|---|---|---|---|
| 4,376,225 A * | 3/1983 | Vora | C07C 5/333 585/658 |
| 4,458,096 A | 7/1984 | Phillips et al. | |
| 6,472,577 B1 | 10/2002 | Zimmermann et al. | |
| 2009/0264692 A1* | 10/2009 | Welch | C07C 5/3332 585/440 |
| 2013/0046122 A1* | 2/2013 | Vermeiren | C10G 69/06 585/251 |
| 2014/0371503 A1* | 12/2014 | Wei | C07C 5/48 585/658 |
| 2017/0297975 A1* | 10/2017 | Radaelli | C08F 10/02 |
| 2019/0352240 A1* | 11/2019 | Jo | C07C 7/12 |
| 2020/0061565 A1* | 2/2020 | Kolios | C01B 32/05 |

FOREIGN PATENT DOCUMENTS

| | | |
|---|---|---|
| KR | 10-2015-0032605 A | 3/2015 |
| KR | 10-2016-0071114 A | 6/2016 |

* cited by examiner

METHOD FOR COLLECTING HARD OLEFIN

TECHNICAL FIELD

The present invention relates to a method for recovering light olefins, and more particularly to a method for recovering light olefins, which can increase production and reduce the basic unit in the process of producing propylene by propane dehydrogenation and also enables two types of products to be obtained from the propane dehydrogenation reaction process by separately collecting ethane and ethylene, i.e., by-products of the propylene production process, and converting the ethane into ethylene, thereby improving the economic efficiency of the process.

BACKGROUND ART

In the petrochemical industry, continuous catalytic conversion is carried out. A moving catalyst dehydrogenation process for hydrocarbons is an important process in the production of light hydrocarbon components, and is an important process in the production of ethylene and propylene. In the moving catalyst dehydrogenation process, the catalyst is continuously circulated between a reactor and a regenerator.

A route for the production of propylene can be obtained by dehydrogenation of propane through a catalytic dehydrogenation reaction. The dehydrogenation catalyst generally includes a noble metal catalyst on an acidic support, such as an alumina, silica alumina, or zeolite support. However, the dehydrogenation reaction is a strong endothermic reaction and requires a high temperature for the reaction to proceed at a satisfactory rate. At the same time, the dehydrogenation reaction needs to be controlled to limit the propane of the degradation to form methane and ethylene, and the ethylene can be hydrogenated by the hydrogen released through the dehydrogenation of propane. In addition, the dehydrogenation process deactivates the catalyst by coking the catalyst. Accordingly, the catalyst needs to be regenerated on a regular basis after a relatively short time of operation, or residence, in the dehydrogenation reactor.

In connection with this, FIG. 1 shows an Oleflex process which is a typical conventional process of separating and recovering propylene from a propane dehydrogenation product. In the Oleflex process as shown in FIG. 1, a propane-containing feed gas stream is preheated to 600 to 700° C. and dehydrogenated in a moving-bed dehydrogenation reactor, thereby obtaining a product gas stream containing propane, propylene and hydrogen as main components.

Meanwhile, the moving-bed reactor is advantageous in that a catalyst can be moved and a continuous catalyst regeneration system can be constructed. As one example of this moving-bed reactor, U.S. Pat. No. 6,472,577 discloses a continuous catalyst regeneration system including a catalyst bed. However, such a conventional fluidized bed dehydrogenation reactor has limitations in that the residence time of the catalyst is short and the conversion rate is low. Since the conversion rate for the dehydrogenation reaction is closely related to the basic unit and economic efficiency of the process, it is urgently required to develop a dehydrogenation reactor capable of improving the conversion rate in order to increase the efficiency of the continuous catalytic reaction-regeneration system.

Meanwhile, ethylene is produced as a by-product in a propane dehydrogenation reaction, and ethylene which is used in a conventional propane dehydrogenation process is used mainly as a fuel for heating furnaces. However, the demand for ethylene in the chemical raw material market recently has increased, and the use of expensive ethylene only as a fuel for heating furnaces is significantly disadvantageous in economic terms. Therefore, it will be advantageous to develop a process that enables ethylene, i.e., a by-product of the propane dehydrogenation process, to be recovered as expensive ethylene.

DISCLOSURE

Technical Problem

The present invention has been conceived to overcome the above-described problems, and an object of the present invention is to provide a method for recovering light olefins, which can increase the total amount of heat supply by supplying reaction heat separately to each of multiple hydrogenation reactor stages and can be operated in a state in which the molar ratio of hydrogen to propane in a feed is 0.4 or less, thereby reducing the basic unit of the process due to a reduction in the hydrogen partial pressure and increasing production due to an increase in yield.

Another object of the present invention is to provide a method for recovering light olefins, which enables two types of products (propylene and ethylene) to be obtained from a propane dehydrogenation reaction process by collecting ethane and ethylene discharged out of the system during the propane dehydrogenation process and converting the ethane into ethylene to produce expensive ethylene, and can adjust the production rate depending on the market situation so that the production equipment can be operated most efficiently.

Technical Solution

One aspect of the present invention for achieving the above-described object is directed to a method for recovering light olefins, including: subjecting a propane-containing feedstock to a dehydrogenation reaction in five serially connected dehydrogenation reactors, wherein the dehydrogenation reaction is performed by feeding the propane-containing feedstock and hydrogen, preheated by two parallel-connected reaction material heaters, into each of the dehydrogenation reactors, and feeding steam separately into each of the dehydrogenation reactors; cooling and compressing a process stream discharged from the last dehydrogenation reactor; quenching the process stream by passage through an ethylene/propylene freezer so that the hydrogen/propane ratio is 0.4 or less; transferring the quenched process stream into a de-ethanizer in which ethane and ethylene from the process stream; separating a process stream containing propane and propylene, separated from the de-ethanizer, by a propane/propylene splitter, thereby obtaining a propylene product; transferring a process stream rich in ethane and ethylene, separated from the de-ethanizer, into a demethanizer in which methane is separated in advance from the process stream; transferring the process stream, from which the methane has been separated, into an acetylene converter ion which acetylene in the process stream is converted into ethane and ethylene; separating the process stream, transferred from the acetylene converter, into ethane and ethylene by passage through an ethane/ethylene splitter, thereby obtaining an ethylene product; and converting the ethane, separated from the ethane/ethylene splitter, into ethylene by an additional reaction in an ethane reactor, thereby obtaining an ethylene product.

Advantageous Effects

According to the method of the present invention, an increase in propylene production and a reduction in the basic unit of the process can be achieved by feeding steam into dehydrogenation reactors. In addition, a reduction in the basic unit of the process and an increase in the total amount of heat supplied can be achieved by supplying reaction heat separately to each of five reactor stages, thereby increasing propylene production.

Furthermore, according to the present invention, an ethylene/propylene freezer is included in a cooling box, whereby it is possible to adjust the molar ratio of hydrogen to propane in the feed fed into the reactor to 0.4 or less, thereby increasing the theoretical yield of the propane dehydrogenation reaction due to a reduction in the hydrogen partial pressure and increasing propylene production due to an increase in the yield of the dehydrogenation reactors.

Moreover, according to the present invention, expensive ethylene can be produced instead of using ethane and ethylene, which are by-products of the propane dehydrogenation process, as inexpensive fuels, whereby two types of products (propylene and ethylene) can be obtained from the propane dehydrogenation reaction process, and thus the production rate of an advantageous product can be increased depending on the market situation, thereby maximizing the economic efficiency of the process.

BEST MODE

Figure 1:
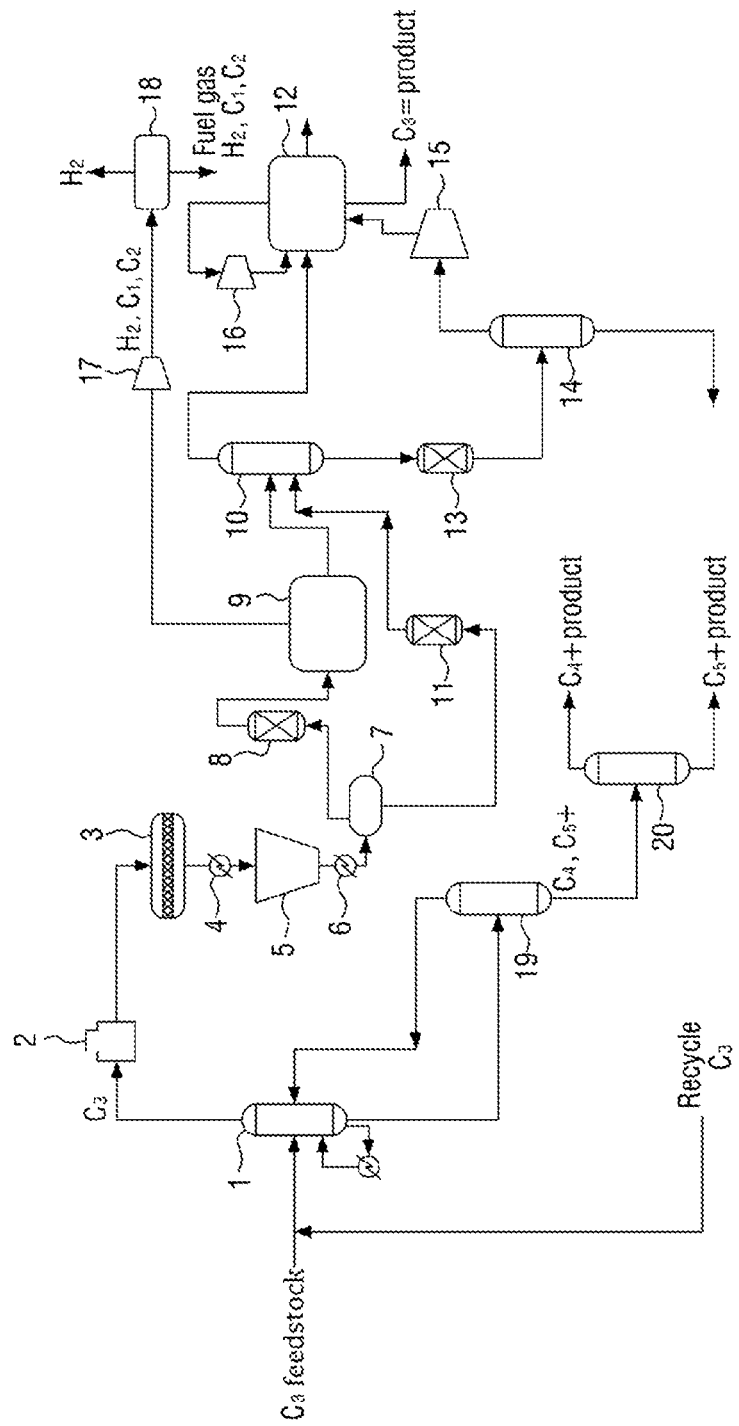
FIG. 1 is a process flow diagram showing a process of producing propylene by propane dehydrogenation according to a conventional art.

The present invention will be described in greater detail below with reference to the accompanying drawings.

Although general terms widely used currently are selected as the terms used herein as much as possible, some terms are randomly selected by the applicant in specific cases. In this case, the meanings of the terms should be determined based on the meanings that are described and used in the detailed description of the present invention, rather than simply based on the names of the terms. Furthermore, the present invention is not limited to the described embodiments, and may be embodied in other forms. Throughout the specification, the same reference symbols designate the same components.

Although the accompanying drawings describe a particular shape of the dehydrogenation reactor of the present invention, this dehydrogenation reactor may have various shapes suitable for particular environments that are performed in particular applications. The broad application of the present invention is not limited to the specific embodiments that will be described below. Furthermore, the numbers in the drawings represent a simple schematic diagram of the multi-stage dehydrogenation reactor of the present invention, and only the major components are shown in the drawings. In addition, heat exchangers, internal heaters, moving pipes for catalyst transfer, pumps, and other similar components are omitted in the drawings. Using these components to modify the described dehydrogenation reactor is known to those skilled in the art and does not depart from the scope and spirit of the appended claims.

It should be understood that various ranges and/or numerical limitations include iterative ranges of like magnitude falling within the expressly stated ranges or limitations.

The term "process stream" used in the present application refers to a reaction product produced through a dehydrogenation reaction. Specifically, it refers to a gas, a liquid, a gas or a liquid containing dispersed solids, or a mixture thereof, which may contain hydrogen, propane, propylene, ethane, ethylene, methane, butane, butylene, butadiene, nitrogen, oxygen, carbon monoxide, or carbon dioxide.

The term "reactor" used in the present application refers to a reaction apparatus in which a reaction gas comes into contact with a catalyst on a catalyst bed.

The term "overhead stream" used in the present application refers to a net overhead stream recovered from a particular zone after recycle of any portion to the zone for recycle or any other reason.

The term "bottom stream" used in the present application refers to a net bottom stream from a particular zone, obtained after recycle of any portion for purposes of reheating and/or reboiling and/or after any phase separation.

The term "light olefins" used in the present application refers to ethylene, propylene, and a mixture thereof.

The term "de-ethanizer" in the present application refers to a column that separates a C1-C2 gas stream containing methane, ethane, ethylene or the like as an overhead stream, separates a C3-C4 gas stream containing propane and propylene as a bottom stream, and sends the C3-C4 gas stream to a propane/propylene splitter.

The "propane/propylene splitter" refers to a column designed to separate propylene from a mixture containing hydrocarbons having 3 or more carbon atoms.

The term "depropanizer" refers to a column designed to separate a hydrocarbon having 4 or more carbon atoms from a mixture containing hydrocarbons having 3 or more carbon atoms.

The term "C4+ hydrocarbon" in the present invention mainly refers to a hydrocarbon having 4 or more carbon atoms.

The term "C5+ hydrocarbon" in the present invention mainly refers to a hydrocarbon having 5 or more carbon atoms.

The term "conversion rate" in the present application refers to the ratio of a propane-containing hydrocarbon to a fed hydrocarbon, which is converted in single pass of the reaction gas through the dehydrogenation reactor.

The term "selectivity" in the present application refers to the moles of propylene which are obtained per mole of propane converted, and is expressed as molar percentage.

Figure 2:
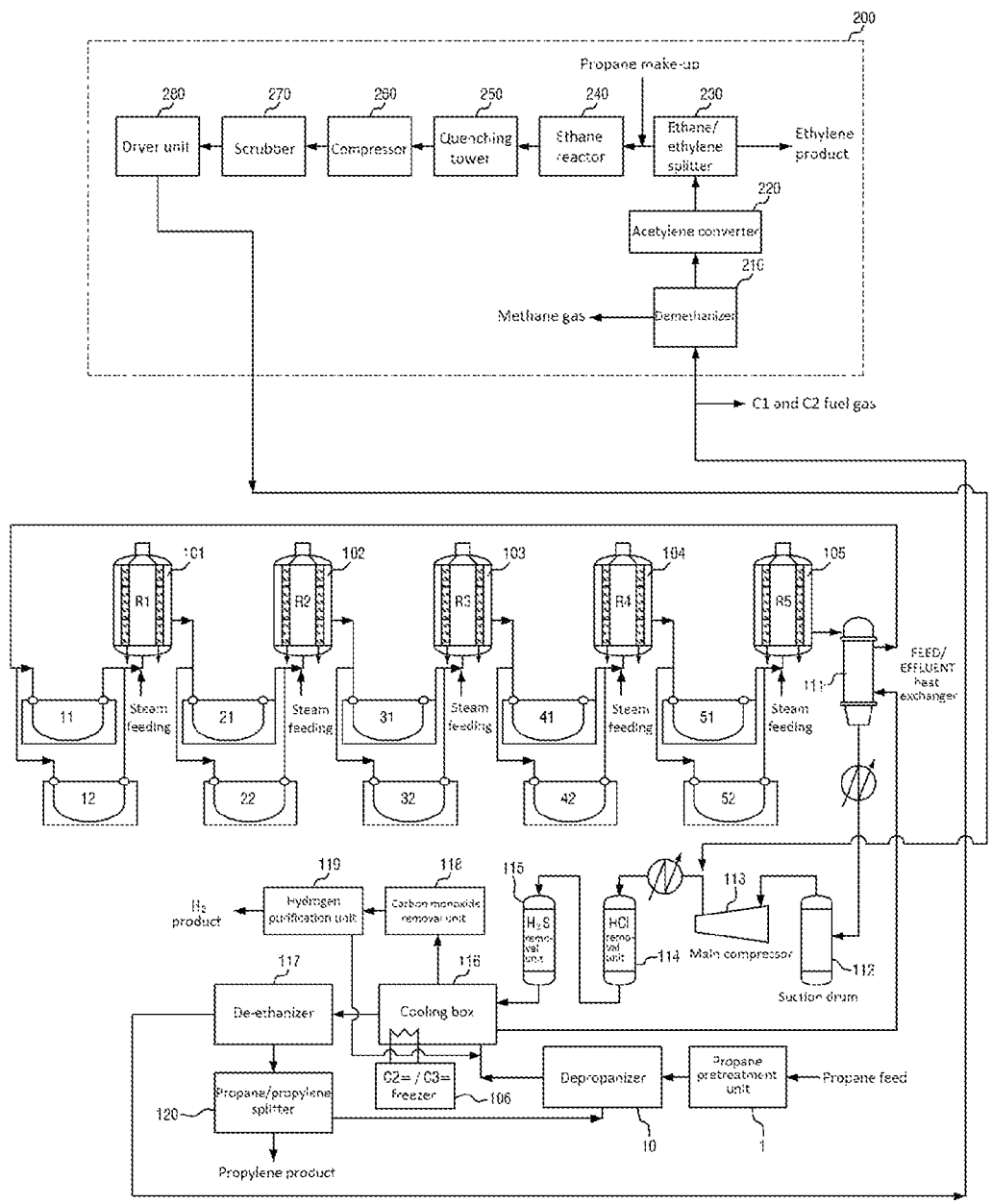
FIG. 2 is a process flow diagram schematically showing a process of producing propylene and ethylene together through a propane dehydrogenation process according to one embodiment of the present invention.

FIG. 2 is a process flow diagram showing a method and apparatus for recovering light olefins according to one embodiment of the present invention.

Referring to FIG. 2, in the present invention, a propane-containing feedstock is subjected to a dehydrogenation reaction in five serially connected dehydrogenation reactors R1 to R5, in which the dehydrogenation reaction is performed by feeding the propane-containing feedstock and hydrogen, preheated by two parallel-connected reaction material heaters, into each of the dehydrogenation reactors, and feeding steam separately into each of the dehydrogenation reactors. A process stream discharged from the last dehydrogenation reactor is cooled and compressed, and then quenched by passage through an ethylene/propylene freezer so that the hydrogen/propane ratio is 0.4 or less. The quenched process stream is transferred into a de-ethanizer in which ethane and ethylene are separated from the process stream. A process stream containing propane and propylene, separated from the de-ethanizer, is separated by a propane/propylene splitter, thereby obtaining a propylene product. Meanwhile, a process stream rich in ethane and ethylene, separated from the de-ethanizer, is transferred into a demethanizer in which methane is separated in advance from the process stream. The methane-separated process stream is transferred into an acetylene converter in which acetylene in the process stream is converted into ethane and ethylene. A process stream transferred from the acetylene converter is separated into ethane and ethylene by passage through an ethane/ethylene splitter, thereby obtaining an ethylene product. The ethane separated from the ethane/ethylene splitter is converted into ethylene by an additional reaction in an ethane reactor, thereby obtaining an ethylene product.

Processes of producing propylene and ethylene through the dehydrogenation process of the present invention will be described below in greater detail.

The method of the present invention includes the step of feeding a propane-containing feedstock, hydrogen and steam dehydrogenation reactors, into followed by dehydrogenation. The dehydrogenation reaction step is performed in five serially connected dehydrogenation reactors, and each of the dehydrogenation reactors includes two parallel-connected heaters configured to heat the feedstock that is fed into each of the reactors. The steam is fed separately into each of the five reactors.

The feed gas stream containing propane is fed into five or more dehydrogenation reactors 101, 102, 103, 104 and 105 in which it is subjected to catalytic dehydrogenation. In this process step, propylene is produced by partially dehydrogenating the propane over a dehydrogenation-active catalyst in the dehydrogenation reactors. Additionally, hydrogen and small amounts of methane, ethane, ethene and C4+ hydrocarbons (n-butane, isobutane, butene) are produced.

In the present invention, the dehydrogenation reaction is performed sequentially in five serially connected reactors, and a process of dehydrogenating propane into propylene is performed by the dehydrogenation reaction in each of the dehydrogenation reactors. The gas stream subjected to the first dehydrogenation reaction is introduced sequentially into the second, third, fourth and fifth dehydrogenation reactors 102, 103, 104 and 105 sequentially connected to the first reactor 101, and is subjected again to the dehydrogenation reaction. That is, in the multi-stage dehydrogenation, a reaction product is introduced into one reactor and subjected to dehydrogenation, and then the reaction product is introduced into the next-stage reactor and subjected to the dehydrogenation process repeatedly depending on the number of the reactors.

The dehydrogenation reactors 101, 102, 103, 104 and 105 that are used in the present invention may be any types of reactors known in the art. For example, the dehydrogenation reactors may be tubular reactors, stirred-tank reactors, or fluidized-bed reactors. As another example, the reactors may also be fixed-bed reactors, tubular fixed-bed reactors, or plate-type reactors.

Referring to FIG. 2, the dehydrogenation reactors in the light olefin recovery apparatus of the present invention include a first reactor 101, a second reactor 102, a third reactor 103, a fourth reactor 104, and a fifth reactor 105. A reactant stream that is a hydrocarbon gas feed is indicated by the solid arrow. The first reactor 101 is fed with either a feed gas stream containing a hydrocarbon (e.g., propane) to be dehydrogenated, or hydrogen, or steam, in which the gas stream that is fed into the first reactor 101 is fed after heating by two parallel-connected reaction material heaters 11 and 12. The feed gas stream is fed directly into the first reactor 101 and subjected to a dehydrogenation reaction in the first reactor, and a first product stream is recovered. Thereafter, the first product stream, steam, and a catalyst used for the reaction in the first reactor 101 are fed into the second reactor 112 having two parallel-connected reaction material heaters 21 and 22 and subjected to a dehydrogenation reaction in the second reactor 102, and a second product stream is recovered from the second reactor 102.

Thereafter, the second product stream, steam, and the catalyst stream used for the reaction in the second reactor 102 are fed into the third reactor 103 having two parallel-connected reaction material heaters 31 and 32 and subjected to a dehydrogenation reaction in the third reactor 103, and a third product stream is recovered from the third reactor 103. The third product stream, steam, and the catalyst stream used for the reaction in the third reactor 103 are fed into the fourth reactor 104 having two parallel-connected reaction material heaters 41 and 42 and subjected to a dehydrogenation reaction in the fourth reactor 104. The fourth product stream, steam, and the catalyst stream used for the reaction in the fourth reactor 104 are fed into the fifth reactor 105 having two parallel-connected reaction material heaters 51 and 52 and subjected to a dehydrogenation reaction in the fifth reactor 115, and a fifth product stream is recovered from the fifth reactor 105 into a product splitter 111. The "process stream" generated in each of the reactors refers to a reaction product produced through the dehydrogenation process. Specifically, the process stream refers to a gas, a liquid, or a gas or a liquid containing dispersed solids, or a mixture thereof, which may contain hydrogen, propane, propylene, ethane, ethylene, methane, butane, butylene, butadiene, nitrogen, oxygen, steam, carbon monoxide, or carbon dioxide.

Since the dehydrogenation reaction is repeated in the five serially connected dehydrogenation reactors as described above, the reaction heat supplied to each reactor may decrease and the load of the reaction material heaters may decrease, thereby increasing reaction selectivity and thus resulting in a reduction in the basic unit of the process. In addition, since all the dehydrogenation reactors are adiabatic reactors, it is possible to perform an additional reaction by the amount of heat supplied from the reaction material heaters disposed in front of one additional reactor, thereby increasing propylene production.

In the present invention, since two parallel-connected reaction materials configured to supply reaction heat are disposed in front of each reactor stage, the load of the reaction material heaters is reduced by half, the temperature uniformity is maintained, and the operating temperature is down-regulated, thereby reducing the basic unit of the process.

In the present invention, steam is fed separately into each of the reactors 101, 102, 103, 104 and 105 in order to prevent the coking of the catalyst. In the method of the present invention, steam is introduced during the dehydrogenation reaction and reacted with hydrocarbons, so that the steam removes coke formed on the catalyst by decomposing the coke into carbon monoxide and hydrogen. Since coke is removed by steam as described above, it is possible to prevent the performance of catalyst active sites from being reduced due to coke formation, thereby improving the long-term performance of the catalyst. In addition, propane may selectively bind to active sites formed on the catalyst surface by by-products, such as ethane, ethylene and methane, thereby increasing the production rate of the main reaction in which propane produces propylene and hydrogen and thus increasing propylene production and reaction selectivity.

After the completion of the dehydrogenation reaction, the product gas stream produced in the fifth reactor 105 is cooled and compressed, and then quenched by passage through a cooling box so that the hydrogen/alkane hydrocarbon ratio in front of the first reactor 1101 may be down-regulated using an ethylene/propylene freezer.

The reaction product discharged from the fifth reactor 105 is heat-exchanged through a heat exchanger 111, and then transferred into a suction drum 112 and separated by boiling point, and a "C5+ hydrocarbon" is separated as a bottom stream.

The overhead stream (gas-phase product) from the suction drum 112 is liquefied through a pressurization and cooling process in a main compressor 113, and then passes sequentially through a hydrogen chloride removal unit 114 and a hydrogen sulfide removal unit 115. Thereafter, the overhead stream is additionally subjected to a cooling and compression process by passage through a cooling box, i.e., a freezing system, and, at the same time, hydrogen containing carbon monoxide is sent to a carbon monoxide removal unit 118, and a hydrocarbon gas stream containing propane and propylene is transferred into a de-ethanizer 117.

Downstream of the main compressor 113 are disposed a hydrogen chloride removal unit 114 configured to remove hydrogen chloride (HCl) generated in the dehydrogenation reaction and catalyst regeneration process, and a hydrogen sulfide removal unit 115 configured to remove a sulfide contaminant discharged from the compressor. This hydrogen chloride removal unit 104 and hydrogen sulfide removal unit 105 may remove contaminants by an adsorbing agent or an adsorbent.

The product obtained from the reactor after the dehydrogenation reaction contains a C4 mixture containing propylene, as well as carbon monoxide, unreacted propane, nitrogen, oxygen, steam, and carbon dioxide. In particular, in the method of the present invention, steam is introduced into the feedstock in order remove coke, and hence coke formed on the catalyst in the reactor reacts with steam ($H_2O$) to produce carbon monoxide and hydrogen ($H_2$). These by-products should be separated and discharged out of the system so as not to be continuously accumulated in the process. Accordingly, in the present invention, a carbon monoxide removal unit 108 configured to remove carbon monoxide is disposed next to the cooling box 116, and a gas stream from which the carbon monoxide has been removed is sent to a hydrogen purification unit 119.

The carbon monoxide removal unit 108 may include hopcalite, which is a mixed oxide of copper-manganese which is highly active for the reaction between carbon monoxide and oxygen. In the presence of the hopcalite, highly toxic hydrogen monoxide reacts with oxygen to form carbon monoxide. In addition, carbon monoxide may be removed by adsorption with an adsorbent composition including a copper oxide, a zinc oxide, and an aluminum oxide.

The process stream obtained from the dehydrogenation reactor may further be subjected to a post-treatment process in order to obtain a highly pure product. In the cooling box 116, a high-temperature hydrocarbon stream supplied from the hydrogen sulfide removal unit 115 is subjected to a cooling and compression process and separated into carbon monoxide-containing hydrogen and a hydrocarbon stream, which are then transferred into a carbon monoxide removal unit 118 and a de-ethanizer 117, respectively.

The ethylene/propylene freezer 106 that may be used in the cooling box 116 may use a propylene-based or ethylene-based solvent as a refrigerant, or if necessary, may perform the same function using other refrigerant. For example, the refrigerant may be one or a mixture of two or more selected from the group consisting of methane, ethylene and propylene. It is to be understood that the propylene-based solvent means propylene or a compound containing propylene, and the ethylene-based solvent means ethylene or a compound containing ethylene.

The molar ratio of hydrogen to a hydrocarbon (propane) in the starting gas mixture that is used in the dehydrogenation process according to the present invention is 0.4 or less. In the present invention, in order to perform the reaction process such that the molar ratio of hydrogen to propane in the feed composition may be down-regulated to a range of 0.4 or less to 0 as described above, the ethylene/propylene freezer 106 is used in the cooling box to meet an energy balance corresponding to the reduction in the hydrogen proportion. Due to this feature, the ratio of hydrogen to propane may be down-regulated, whereby the reaction yield may be increased by about 5% to 10% compared to a conventional process, and the reaction selectivity may also be increased by up to 2-5%.

Prior to the process of the de-ethanizer 101, components, such as hydrogen and carbon monoxide, which have the lowest boiling point among the overall process, are separated from the cooling box 116, pressurized, and then recovered as hydrogen from the hydrogen purification unit 118. Meanwhile, a propylene-containing process stream that passed through the cooling box 116 and the de-ethanizer 117 is separated into propane and a C4 mixture in the propane/propylene splitter 120, and the propylene is purified and recovered.

In a propane pretreatment unit 1, impurities, such as water, metal impurities, and carbon monoxide, are removed from the propane feed, and a propane gas stream containing a very small amount of a C4 mixture is transferred into a depropanizer 10. In the depropanizer 122, butane, butylene, butadiene, and the like, which cause coke formation by a polymerization reaction on the catalyst located inside the reactor, are removed before the component contained in the reaction gas is fed into the first dehydrogenation reactor 101. A high-purity propane stream supplied to the depropanizer 10 is mixed with hydrogen supplied from a hydrogen purification unit 119, and then it is heated by low-temperature heat exchange in the cooling box 116, and transferred to a heat exchanger 111 in which it is heated by heat exchange. The heated stream is further heated by the reaction material heaters 11 and 12 and is introduced again into the first reactor 101.

The process stream, from which impurities have been removed in the hydrogen chloride removal unit 114 and the hydrogen sulfide removal unit 115, is further liquefied by compression in the cooling box 116. The cooling box 116 may include a heat removal unit (not shown) configured to additional heat, which is generated during compression, so that the process stream may be operated in the subsequent de-ethanizer 117. The heat removal unit may also remove heat by heat exchange with either the hydrogen gas recycled from the hydrogen chloride removal unit 114 and the hydrogen sulfide removal unit 115 in the process, or a low-temperature gas such as the liquefied propane separated from the depropanizer 10, or a liquid reactant. The liquefied process stream is separated in the de-ethanizer 17, and methane, ethane and ethylene, which are by-products, are introduced into the demethanizer 210, and the remaining process stream, from which the by-products have been removed, are introduced into a propane/propylene splitter 120. In the propane/propylene splitter 120, propylene is separated as an overhead stream, and a C3-C4 gas stream containing propane is separated as a bottom stream and sent to the depropanizer 10. Unreacted propane, butane and butylene in the process stream introduced into the propane/propylene splitter 120 are separated by a column, and a pure propylene product is obtained.

The separated unreacted propane is supplied to the front end of the first dehydrogenation reactor 101 through a propane recycle pipeline, which is an inert recycle line, and is recycled as a feed propane gas. At this time, it is also possible to perform a process of capturing a hydrogen gas separately from the process stream, which passed through the hydrogen chloride removal unit 114 and the hydrogen sulfide removal unit 115, and increasing the purity of the hydrogen gas in a pressure swing adsorption (PSA) unit (not shown). The hydrogen gas having increased purity is sold commercially or sent to the first dehydrogenation reactor 101 and recycled as a reactant gas. The unreacted propane separated from the propane/propylene splitter 120 is transferred to the front end of the depropanizer 10 through a propane recycle pipeline and recycled as a feed propane gas.

The method of the present invention may produce propylene and hydrogen through the propane dehydrogenation reaction, and at the same time, may also produce expensive ethylene using ethane and ethylene, which are by-products. In the present invention, a process of recovering ethylene during the propane dehydrogenation process may include passing a process stream containing methane, ethane and ethylene, which are by-products generated in the de-ethanizer 117, through the demethanizer 210 to separate the methane first, transferring the process stream, from which the methane has been separated, into the acetylene converter 220 to convert acetylene in the process stream to ethane and ethylene, passing the process stream, separated from the acetylene converter 220, through an ethane/ethylene splitter 230 to separate ethane from ethylene, converting the separated ethane to ethylene by an additional reaction in an ethane reactor 240, cooling the process stream, which passed through the ethane reactor 240, by passage through a quenching tower 250, compressing the cooled process stream by a compressor 260, neutralizing the compressed process stream by passage through a scrubber 270, and then injecting the neutralized process stream between the main compressor of the existing dehydrogenation process and the hydrogen chloride removal unit 114 so that the dehydrogenation process is continuously performed.

After the neutralizing step, the step of removing impurities, such as water, hydrogen chloride and hydrogen sulfide, by dehydration in a dryer unit 280, may further be included. That is, in the method of the present invention, the process of recovering ethylene is configured such that ethylene produced in the ethane reactor 240 after passage through the de-ethanizer, the demethanizer 120 and the ethane/ethylene splitter 240 is separated again. When ethane collected by passage through the ethane/ethylene splitter 230 is additionally reacted in the ethane reactor 240, the ethane separated after the propane dehydrogenation reaction may be converted into ethylene, thereby producing additional ethylene.

The process of recovering ethylene during the propane dehydrogenation process will be described below in greater detail.

First, the process stream that passed through the de-ethanizer 117 contains methane, ethane and ethylene as reaction by-products. Such reaction by-products are passed through the demethanizer 210, and the methane is separated in advance by the column. The process conditions are a temperature of −129° C. to 52° C. and a pressure of 5 kgf/cm$^2$ to 50 kgf/cm$^2$. The separated methane gas has, for example, a temperature of 40° C. and a pressure of 3.2 kgf/cm$^2$. The methane separated by the demethanizer 210 may be used as a heating fuel.

The process stream, from which the methane has been separated, is brought into contact with hydrogen in the acetylene converter 220 in which acetylene in the process stream is converted into ethane and ethylene, thereby forming a process stream which is lean or substantially free of acetylene. The process stream that is lean of acetylene is immediately passed through the ethane/ethylene splitter 230 in which it is separated into an ethane overhead stream and an ethylene bottom stream. The process conditions are a temperature of −60° C. to 40° C. and a pressure of 10 kgf/cm$^2$ to 80 kgf/cm$^2$. For example, the separated ethylene gas has a temperature of 25° C. and a pressure of 40 kgf/cm$^2$.

The ethane separated from the ethane/ethylene splitter 230 is additionally reacted in the ethane reactor 240, so that the ethane is converted into ethylene. The reaction of converting ethane to ethylene in the ethane reactor 240 does not particularly require a catalyst. Alternatively, a catalyst may also be used to convert the ethane to ethylene. The catalyst that is used in this case is not particularly limited, and may be, for example, a platinum catalyst. The process conditions of the ethane reactor 240 are a reaction temperature of 650° C. to 950° C. and a pressure of 0.1 kgf/cm$^2$ to 10 kgf/cm$^2$. In one embodiment, the ethane gas that is introduced in the ethane reactor 240 may have a temperature of −30° C. and a pressure of 1.2 kgf/cm$^2$. In addition, immediately in front of the ethane reactor 240, a heater unit (not shown) configured to supply heat necessary for the reaction occurring in the ethane reactor 2409 may be disposed. Furthermore, in front of the ethane reactor 240, an additional feed gas line configured to supply propane may be disposed to control the ratio of ethylene production to propylene production.

The process stream whose temperature has been increased by the reaction of converting ethane to ethylene in the ethane reactor 240 is cooled in the quenching tower 250. The reaction product obtained from the ethane reactor 240 may be in the form of high-temperature gas, and thus needs to be cooled before being fed again into the main dehydrogenation process apparatus. A cooling method that is used in the cooling step is not particularly limited. For example, a cooling method of brining a cooling solvent into direct contact with the reaction product may be used, or a cooling method of brining a cooling solvent into indirect contact with the reaction product may also be used.

Thereafter, the cooled process stream is compressed in a compressor 260 and passed through a scrubber 270 in which the catalyst and additional gases are neutralized. The compressor 260 reduces the pressure difference from the pressure at a supply position so that the reactant stream produced in the ethane reactor 240 may be smoothly supplied to the rear end of the main compressor 113 via the scrubber 270 and the dryer unit 280. In addition, the reactant stream that passed through the compressor 260 is neutralized by caustic wash treatment in the scrubber 270 in order to remove $Cl_2$ gas produced by a Cl-containing catalyst during process recycling.

Thereafter, the neutralized process stream is passed through the dryer unit 280 in which impurities, such as water, hydrogen chloride and hydrogen sulfide, are removed from the process stream. The process conditions are a temperature of −40° C. to 100° C. and a pressure of 0.01 kgf/cm² to 60 kgf/cm². After the neutralizing step or the drying step, the process stream is injected between the main compressor 113 and the hydrogen chloride removal unit 114 in the existing dehydrogenation process. The process stream that is supplied to the rear end of the main compressor 113 may contain propane, propylene, ethane, ethylene, methane and hydrogen gases, and in one embodiment, the process stream may have a temperature of 30° C. and a pressure of 0.1 kgf/cm².

According to the present invention, the ethane reactor 240 is disposed in the rear of the ethane/ethylene splitter 230, and thus the concentration of ethylene that is introduced into the de-ethanizer 117 during recycling production increases. Accordingly, the ethylene produced may be separated in advance, so that catalyst coking in the ethane reactor 240 may be prevented and ethylene may be prevented from being lost by ethylene side reactions. In addition, since ethylene that passed through the ethane/ethylene splitter 230 and ethylene produced in the ethane reactor 240 are separated again, ethane which is a by-product of the propane dehydrogenation process may be mostly converted into ethylene without being used as an inexpensive fuel, so that expensive ethylene may be produced, thereby improving the economic efficiency of the process. As a result, the product of the propane dehydrogenation may be diversified from a propylene single product into propylene and ethylene, so that the operating conditions of the propylene dehydrogenation reactors and the operating conditions of the de-ethanizer may be adjusted depending on the market situation.

While the present invention has been described in detail in connection with the preferred embodiments of the present invention, it will be apparent that the present invention is not limited to the above-described embodiments and those skilled in the art will appreciate that many modifications may be made without departing from the scope of the technical spirit of the present invention. Therefore, the true scope of the present invention should be defined based on the appended claims and the equivalents thereof. For example, although the propane dehydrogenation reaction for producing propylene has been mainly described in detail above, the disclosure of the present application may be applied to dehydrogenation reactions that convert alkanes containing 2 or more carbon atoms, for example, ethane, n-butane, isobutene and pentane, to the corresponding olefins, as understood by those skilled in the art through the disclosure of the present application.

The invention claimed is:

1. A method for recovering light olefins, the method comprising:
    subjecting a propane-containing feedstock to a dehydrogenation reaction in five serially connected dehydrogenation reactors, wherein the dehydrogenation reaction is performed by feeding the propane-containing feedstock and hydrogen, preheated by two parallel-connected reaction material heaters, into each of the dehydrogenation reactors, and feeding steam separately into each of the dehydrogenation reactors;
    cooling and compressing a process stream discharged from the last dehydrogenation reactor;
    quenching the process stream by passage through an ethylene/propylene freezer so that a hydrogen/propane ratio is 0.4 or less;
    transferring the quenched process stream into a de-ethanizer in which ethane and ethylene are separated from the process stream;
    separating a process stream containing propane and propylene, separated from the de-ethanizer, by a propane/propylene splitter, thereby obtaining a propylene product;
    transferring a process stream rich in ethane and ethylene, separated from the de-ethanizer, into a demethanizer in which methane is separated in advance from the process stream;
    transferring the process stream, from which the methane has been separated, into an acetylene converter in which acetylene in the process stream is converted into ethane and ethylene;
    separating the process stream, transferred from the acetylene converter, into ethane and ethylene by passage through an ethane/ethylene splitter, thereby obtaining an ethylene product; and
    converting the ethane, separated from the ethane/ethylene splitter, into ethylene by an additional reaction in an ethane reactor, thereby obtaining an ethylene product.

2. The method of claim 1, further comprising:
    cooling the process stream, which has passed through the ethane reactor, by passage through a quenching tower, compressing the cooled process stream by a compressor, neutralizing the compressed process stream by passage through a scrubber; and
    recycling the neutralized process stream to the dehydrogenation process by introducing the neutralized process stream into a rear end of a main compressor in the propane dehydrogenation process.

3. The method of claim 1, further comprising:
    after cooling and compressing the process stream discharged from the last dehydrogenation reactor and before passing the process stream through the ethylene/propylene freezer, removing hydrogen chloride and hydrogen sulfide ($H_2S$) from the process stream.

4. The method of claim 1, further comprising:
    after quenching the process stream by passage through the ethylene/propylene freezer, adsorbing and removing carbon monoxide (CO) from a process stream coming out from a cooling box, and then transferring the process stream to a hydrogen purification step.

5. The method of claim 1, further comprising:
    pretreating the propane feed, and then transferring the pretreated propane feed into a depropanizer in which at least a portion of C4+ hydrocarbons is separated as a bottom stream and a first purified propylene-containing product containing C3 or lighter hydrocarbons and hydrogen is separated as an overhead stream.

6. The method of claim 2, further comprising:
    drying the process stream, neutralized by neutralizing the compressed process stream, in a dryer unit to remove impurities.

7. The method of claim 6, further comprising:
    capturing a hydrogen gas separately from the process stream that has passed through the dryer unit; increasing a purity of the hydrogen gas in a pressure swing adsorption (PSA) unit, and
    recovering the hydrogen gas.

8. The method of claim 1, further comprising:
    transferring unreacted propane, separated from the propane/propylene splitter, to a front end of the dehydrogenation reactor through a propane recycle pipeline, and recycling the transferred unreacted propane as a feed propane gas.

9. The method of claim 1, wherein the methane in separating the methane in advance in the demethanizer has a temperature of −20° C. to 80° C. and a pressure of 0.4 kgf/cm$^2$ to 8 kgf/cm$^2$.

10. The method of claim 1, wherein a heat unit is disposed in front of the ethane reactor to supply heat necessary for the reaction in the ethane reactor.

11. The method of claim 1, wherein process conditions of the ethane reactor are a reaction temperature of 650° C. to 950° C. and a pressure of 0.1 kgf/cm$^2$ to 10 kgf/cm$^2$.

12. The method of claim 1, wherein a separate feed gas line is disposed in front of the ethane reactor, and
wherein the method further comprises:
controlling a ratio of ethylene production to propylene production by supplying propane through the feed gas line.

13. A method for recovering light olefins, the method comprising:
subjecting a propane-containing feedstock to a dehydrogenation reaction in serially connected at least two dehydrogenation reactors, wherein the dehydrogenation reaction is performed by feeding the propane-containing feedstock and hydrogen, preheated by parallel-connected reaction material heater(s), into each of the dehydrogenation reactors, and feeding steam separately into each of the dehydrogenation reactors;
cooling and compressing a process stream discharged from the last dehydrogenation reactor;
quenching the process stream by passage through an ethylene/propylene freezer so that a hydrogen/propane ratio is 0.4 or less;
transferring the quenched process stream into a de-ethanizer in which ethane and ethylene are separated from the process stream;
separating a process stream containing propane and propylene, separated from the de-ethanizer, by a propane/propylene splitter, thereby obtaining a propylene product;
transferring a process stream rich in ethane and ethylene, separated from the de-ethanizer, into a demethanizer in which methane is separated in advance from the process stream;
transferring the process stream, from which the methane has been separated, into an acetylene converter in which acetylene in the process stream is converted into ethane and ethylene;
separating the process stream, transferred from the acetylene converter, into ethane and ethylene by passage through an ethane/ethylene splitter, thereby obtaining an ethylene product; and
converting the ethane, separated from the ethane/ethylene splitter, into ethylene by an additional reaction in an ethane reactor, thereby obtaining an ethylene product.

* * * * *